United States Patent
Everman et al.

(10) Patent No.: US 12,274,545 B2
(45) Date of Patent: Apr. 15, 2025

(54) METHODS AND SYSTEMS FOR DETECTION OF ATELECTASIS IN FLIGHT

(71) Applicant: GMECI, LLC, Beavercreek, OH (US)

(72) Inventors: Bradford R. Everman, Haddonfield, NJ (US); Brian Scott Bradke, Brookfield, VT (US)

(*) Notice: Subject to any disclaimer, the term of this patent is extended or adjusted under 35 U.S.C. 154(b) by 0 days.

(21) Appl. No.: 17/731,996

(22) Filed: Apr. 28, 2022

(65) Prior Publication Data

US 2023/0346255 A1    Nov. 2, 2023

(51) Int. Cl.
*A61B 5/091* (2006.01)
*A61B 5/00* (2006.01)

(52) U.S. Cl.
CPC ............ *A61B 5/091* (2013.01); *A61B 5/486* (2013.01); *A61B 5/6803* (2013.01); *A61B 5/746* (2013.01); *A61B 2503/20* (2013.01); *A61B 2560/0242* (2013.01); *A61B 2562/0219* (2013.01)

(58) Field of Classification Search
CPC ........... A61B 5/6803; A61B 5/746; A61B 2560/0242; A61B 5/091; A61B 5/08; A61B 5/0836; A61B 5/486; A61B 2503/20; A61B 5/7264; A61B 5/7275; B64D 13/00; B64D 45/0056
See application file for complete search history.

(56) References Cited

U.S. PATENT DOCUMENTS

| | | |
|---|---|---|
| 2,390,233 A | 12/1945 | Akerman et al. |
| 3,555,886 A | 1/1971 | Thornton |
| 4,651,728 A | 3/1987 | Gupta et al. |
| 5,226,410 A | 7/1993 | Fournol |
| 7,040,319 B1 * | 5/2006 | Kelly ............... B64D 10/00 128/204.22 |
| 7,246,620 B2 | 7/2007 | Conroy, Jr. |
| RE40,402 E | 6/2008 | Leonhardt et al. |

(Continued)

FOREIGN PATENT DOCUMENTS

| | | | |
|---|---|---|---|
| JP | 2003511143 A * | 3/2003 | |
| WO | WO-0156454 A2 * | 8/2001 | ........... A61B 5/0002 |
| WO | 2021000021 | 1/2021 | |

OTHER PUBLICATIONS

John B. West, A strategy for in-flight measurements of physiology of pilots of high-performance fighter aircraft, Jul. 1, 2013.

(Continued)

*Primary Examiner* — Patrick Fernandes
*Assistant Examiner* — Jonathan E. Cooper
(74) *Attorney, Agent, or Firm* — Caldwell Intellectual Property Law

(57) ABSTRACT

Aspects relate to methods and systems for detection of atelectasis in flight. An exemplary system includes at least an exhalation sensor configured to detect at least an exhalation parameter of a flight crew member, at least an inhalation sensor configured to detect at least an inhalation parameter of the flight crew member, at least an environmental sensor configured to detect at least an environmental parameter of a cabin within which the flight crew member is housed, and a computing device configured to determine a likelihood of atelectasis for the flight crew member as a function of the at least an exhalation parameter, the at least an inhalation parameter, and the at least an environmental parameter and generate a dosing schedule as a function of the likelihood of atelectasis.

14 Claims, 11 Drawing Sheets

(56) References Cited

U.S. PATENT DOCUMENTS

| | | |
|---|---|---|
| 7,591,789 B2 | 9/2009 | Bryant |
| 8,517,016 B2 | 8/2013 | Caro et al. |
| 10,108,325 B2* | 10/2018 | Hay .................... G06T 7/0016 |
| 10,561,863 B1* | 2/2020 | Dashevsky .............. A61B 5/01 |
| 10,786,693 B1 | 9/2020 | Opperman et al. |
| 2003/0065274 A1* | 4/2003 | Mault .................... A61B 5/087 |
| | | 600/531 |
| 2004/0206352 A1* | 10/2004 | Conroy, Jr. ........ A61B 5/14551 |
| | | 128/204.23 |
| 2009/0228161 A1* | 9/2009 | Botargues ............ G05D 1/0055 |
| | | 701/11 |
| 2012/0022723 A1* | 1/2012 | Botargues ............ G05D 1/0055 |
| | | 701/4 |
| 2012/0136232 A1* | 5/2012 | Jeong .................. A61B 5/0002 |
| | | 600/386 |
| 2013/0079658 A1* | 3/2013 | Cardoso ............... G01N 33/497 |
| | | 600/532 |
| 2014/0190481 A1 | 7/2014 | Jam |
| 2015/0196245 A1* | 7/2015 | Peake ...................... A62B 7/14 |
| | | 128/202.13 |
| 2017/0325727 A1* | 11/2017 | Buza ...................... A61B 5/742 |
| 2018/0098739 A1 | 4/2018 | Freeman et al. |
| 2018/0126099 A1* | 5/2018 | Verjus ............... A61M 15/0086 |
| 2019/0033862 A1* | 1/2019 | Groden ................ G08G 5/0086 |
| 2020/0129714 A1 | 4/2020 | Jafari et al. |
| 2021/0059616 A1* | 3/2021 | Abrol ................... A61B 5/0022 |
| 2023/0405248 A1* | 12/2023 | Alexander ........ A61M 16/0051 |

OTHER PUBLICATIONS

N/A, Nasa Engineering and Safety Center Technical Assessment Report vol. I F/A-18 and E/A-18 Fleet Physiological Episodes, Aug. 14, 2017.

Ross D. Pollock, et al., Indices of acceleration atelectasis and the effect of hypergravity duration on its development, Apr. 13, 2020.

* cited by examiner

METHODS AND SYSTEMS FOR DETECTION OF ATELECTASIS IN FLIGHT

FIELD OF THE INVENTION

The present invention generally relates to the field of physiological sensing devices. In particular, the present invention is directed to methods and systems for detection of atelectasis in flight

BACKGROUND

During flight pilots and other crew members may experience low cabin pressure resulting from high altitude flight, as well as excessive G-forces. In some cases, these conditions can result in atelectasis or the collapse of at least a portion of a lung. Atelectasis can result in less effective oxygen intake and carbon dioxide evacuation during breathing, which can lead to serious physiological impairment.

SUMMARY OF THE DISCLOSURE

In an aspect a system for detection of atelectasis in flight includes at least an exhalation sensor configured to detect at least an exhalation parameter of a flight crew member, at least an inhalation sensor configured to detect at least an inhalation parameter of the flight crew member, at least an environmental sensor configured to detect at least an environmental parameter of a cabin within which the flight crew member is housed, and a computing device configured to determine a likelihood of atelectasis for the flight crew member as a function of the at least an exhalation parameter, the at least an inhalation parameter, and the at least an environmental parameter and generate a dosing schedule as a function of the likelihood of atelectasis.

In another aspect a method for detection of atelectasis in flight includes detecting, using at least an exhalation sensor, at least an exhalation parameter of a flight crew member, detecting, using at least an inhalation sensor, at least an inhalation parameter of the flight crew member, detecting, using at least an environmental sensor, at least an environmental parameter of a cabin within which the flight crew member is housed, determining, using a computing device, a likelihood of atelectasis for the flight crew member as a function of the at least an exhalation parameter, the at least an inhalation parameter, and the at least an environmental parameter, and generating, using the computing device, a dosing schedule as a function of the likelihood of atelectasis.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for detection of atelectasis in flight. In an embodiment, an exhalation parameter, an inhalation parameter, and/or an environmental parameter may be used to determine a likelihood of atelectasis.

Aspects of the present disclosure can be used to determine a dosing schedule (of high-altitude flight and/or high G-force flight maneuvers) for a member of a flight crew, which will likely prevent atelectasis. Aspects of the present disclosure can also be used to determine a recompression schedule. This is so, at least in part, because atelectasis from flight may be reversed by prescribed recompression of an affect flight crew member.

Exemplary embodiments illustrating aspects of the present disclosure are described below in the context of several specific examples.

Figure 1:
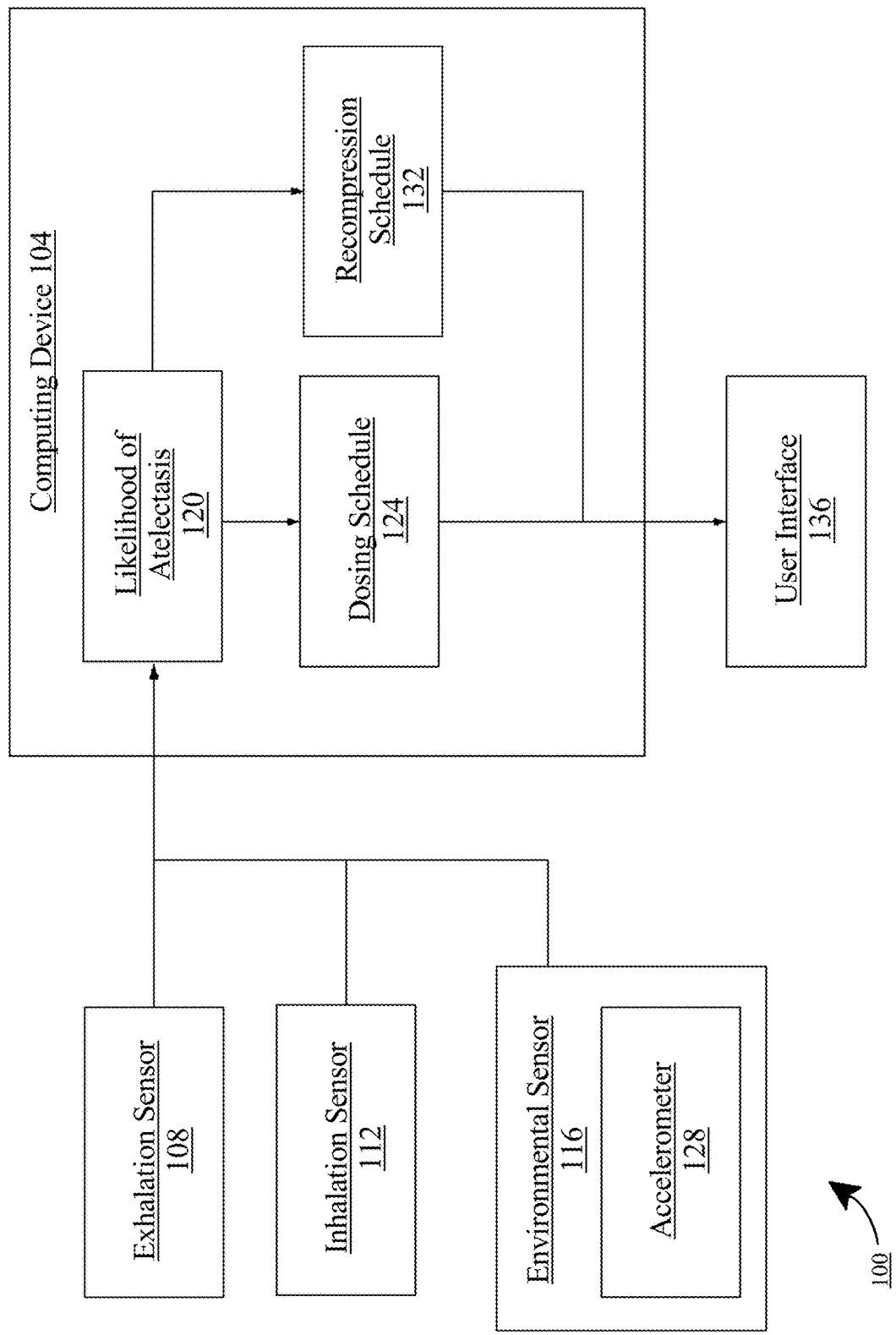
FIG. 1 is a block diagram illustrating an exemplary system for detecting atelectasis in flight.

Referring now to FIG. 1, an exemplary embodiment of a system 100 for detection of atelectasis in flight is illustrated. As used in this disclosure, "atelectasis" refers to a complete or partial collapse of a lung or a portion of a lung. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof.

Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 may include at least an exhalation sensor 108. Exhalation sensor 108 may include any exhalation sensor described in this disclosure, including with reference to FIGS. 2-4. In some cases, at least an exhalation sensor may be configured to detect at least an exhalation parameter of a flight crew member. As used in this disclosure, a "flight crew member" is any person within an aircraft in flight, such as without limitation a co-pilot, pilot, navigator, and the like. As used in this disclosure, a "exhalation sensor" is a sensor configured to detect an exhalation parameter representative of a phenomenon associated with exhalation, for example without limitation exhalation of a user. Exhalation parameter may be associated with at least a portion of an expirate. As used in this disclosure, "expirate" fluid exhaled during an exhalation of breath, such as without limitation air. In some embodiments, at least an exhalation parameter may include expirate volume. Expirate volume may include a volume of a single expirate and/or a flow rate of expirate. In some embodiments, at least an exhalation parameter may include expirate carbon dioxide concentration. Expirate carbon dioxide concentration may include any carbon dioxide concentration measurement, including without limitation partial pressure, tidal carbon dioxide concentration, and the like.

With continued reference to FIG. 1, system 100 may include at least an inhalation sensor 112. Inhalation sensor may include any inhalation sensor described in this disclosure, including with reference to FIG. 5. In some cases, at least an inhalation sensor 112 may be configured to detect at least an inhalation parameter of flight crew member. As used in this disclosure, a "inhalation sensor" is a sensor configured to detect an inhalation parameter representative of a phenomenon associated with inhalation, for example without limitation inhalation of a user. Inhalation sensor may include any inhalation sensor described in this disclosure. In some cases, inhalation sensor may include an inspirate sensor. Inhalation parameter may be associated with at least a portion of an inspirate. As used in this disclosure, "inspirate" is fluid inhaled during an inhalation of breath, such as without limitation air. In some embodiments, at least an inhalation parameter comprises inspirate volume. Inspirate volume may include a volume of a single inspirate and/or a flow rate of inspirate. In some embodiments, at least an inhalation parameter comprises inspirate oxygen concentration. Inspirate oxygen concentration may include any oxygen concentration measurement, including without limitation partial pressure, tidal oxygen concentration, and the like.

With continued reference to FIG. 1, system 100 may include at least an environmental sensor 116 configured to detect at least an environmental parameter of a cabin. Environmental sensor may include any environmental sensor described in this disclosure, including with reference to FIGS. 2-4. As used in this disclosure, a "cabin" is a portion of an aircraft that is configured to house a flight crew member during flight. As used in this disclosure, an "environmental sensor" is a sensor configured to detect an environmental parameter representative of a phenomenon associated with an environment, for example without limitation an environment within which a user is in such as a cabin. Environmental sensor 116 may include any sensor described in this disclosure, including for example an inertial measurement unit, a gas concentration sensor, a pressure sensor, and the like. Environmental sensor 116 may be configured to detect an environmental parameter associated with an environment of flight crew member. As used in this disclosure, a "environmental parameter" is at least an element of data representative of a phenomenon associated with an environment, for example without limitation an environment within which a user is in such as a cabin. In some embodiments, environmental sensor 116 may include a motion sensor. As used in this disclosure, a "motion sensor" is a sensor configured to detect a motion parameter representative of a phenomenon associated with motion, for example without limitation motion of a user an/or vehicle. Non-limiting exemplary motion sensors include inertial measurement units, accelerometers, gyroscopes, and the like. In some cases, at least a motion sensor may be configured to detect at least a motion parameter. As used in this disclosure, a "motion parameter" is at least an element of data representative of a phenomenon associated with motion, for example without limitation motion of a user and/or a vehicle.

Still referring to FIG. 1, in some embodiments, one or more of at least an exhalation sensor 108, at least an inhalation sensor 112, and/or at least an environmental sensor 116 may include a plurality of sensors. In some cases, a plurality of sensors may include at least a master sensor configured to detect at least a master parameter and at least a slave sensor configured to detect at least a slave parameter. As used in this disclosure, a "master" is an attributive which describes a particular component of a plurality of component, where the particular, master, component is prioritized over and/or controls other (slave) components within the plurality of components. As used in this disclosure, a "slave" is an attributive which describes at least a particular component of a plurality of components, where the at least a particular, slave, component is posterioritized after and/or controlled by another (master) device within the plurality of components. Computing device 104 may receive at least a master parameter and at least a slave parameter. Computing device 104 may merge at least a parameter as a function of at least a master parameter and at least a slave parameter. For example, in some cases, system 100 may additionally include a master inhalation sensor configured to detect a master inhalation parameter; and a slave inhalation sensor configured to detect a slave inhalation parameter; and wherein, at least a computing device 104 may be further configured to merge at least an inhalation parameter as a function of the master inhalation parameter and the slave inhalation parameter.

Still referring to FIG. 1, in some cases, merging master and slave parameters and/or any plurality of parameters may include comparing a difference between the parameters, such as without limitation a percent difference. In some cases, a difference between parameters may be calculated thus:

$$\frac{\text{Master} - \text{Slave}}{(\text{Master} + \text{Slave})^2}$$

According to the above equation, a negative number means slave parameter was higher than master and vice versa In some cases, merging may include filtering one or more parameters having bad data, such as without limitation out of range parameters. For example, if a parameter is out of range, it may not be included in merging or any other processes. In some cases, a parameter may be determined to have bad data if it does not exhibit an appropriate amount of variability, for example over time. For example, referring to an inhalation parameter, suspected bad data may include an O2 concentration value "pegged at 100%" with no variability. If a parameter is determined to have bad data, corresponding sensor 108, 112, 116, and/or 128 may be flagged. According to some embodiments, bad data detecting and sensor flagging may be performed in situ and/or prior to use of system 100.

Still referring to FIG. 1, in some cases, merging parameters may include averaging. In some cases, merging parameters may be performed as a function of difference between parameters. For example, in some cases, parameters may only be merged when the plurality of parameters have a difference no greater than a certain threshold (e.g., 20%, 10%, 5%, 1%, and the like). In some cases, a parameter from a plurality of parameters may not be merged but may simply be selected for use. For example, in some embodiments, at initialization a used parameter value may be set equal to master parameter value.

Still referring to FIG. 1, in an exemplary embodiment, an inhalation parameter, inhalation rate, may be selected for use from a plurality of parameters according to a following sequence. (1) a default pulse rate may be set to master inhalation rate. (2) If percent difference between master inhalation rate and at least a slave inhalation rate is greater than a certain threshold (e.g., 20%), then do not merge the parameters and instead select a parameter depending upon parameter value. (3) If an inhalation rate has bad data, use another inhalation rate without bad data. In some cases, inhalation rate is not merged, instead a single inhalation sensor 112 may be used to provide inhalation rate, until the inhalation rate is found to possess bad data and another inhalation sensor 112 may be user. Any parameter described in this disclosure may be represented as a signal.

Still referring to FIG. 1, As used in this disclosure, a "signal" is any intelligible representation of data, for example from one device to another. A signal may include an optical signal, a hydraulic signal, a pneumatic signal, a mechanical, signal, an electric signal, a digital signal, an analog signal and the like. In some cases, a signal may be used to communicate with a computing device 104, for example by way of one or more ports. In some cases, a signal may be transmitted and/or received by a computing device 104 for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing device 104. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

Still referring to FIG. 1, in some cases, system 100 may perform one or more signal processing steps on a sensed characteristic. For instance, system 100 may analyze, modify, and/or synthesize a signal representative of at least a parameter in order to improve the signal, for instance by improving transmission, storage efficiency, or signal to noise ratio. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which varying continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 1, computing device 104 may be in communication with one or more of exhalation sensor 108, inhalation sensor 112, and/or environmental sensor 116. Computing device 104 may be configured to determine a likelihood of atelectasis 120, for instance for flight crew member. As used in this disclosure, "likelihood of atelectasis" is a quantified measure of a prediction that a flight crew member will experience atelectasis. A likelihood of atelectasis may include a probability, for instance as expressed by a percentage or a fraction. In some cases, computing device 104 may be configured to determine a likelihood of atelectasis 120 as a function of at least an exhalation parameter, at least an inhalation parameter, and at least an environmental parameter. In some embodiments, determining likelihood of atelectasis 120 may additionally include comparing a detected environmental parameter with an environmental parameter threshold. As used in this disclosure, an "environmental parameter threshold" is a certain environmental parameter value. In some cases, environmental parameter threshold may be predetermined. In some cases, environmental parameter threshold may be determined, using computing device, as a function of detected parameters or a likelihood of atelectasis, and may change over time. In some cases, environmental parameter threshold may be compared to detected environmental parameters, using computing device. According to some embodiments, computing device 104 may be configured to determine a likelihood of atelectasis using at least a machine-learning process. Machine-learning process may include any machine-learning process, for example explained in reference to FIGS. 6-9. Alternatively or additionally, determination of a likelihood of atelectasis 120 may include pre-programmed conditions or algorithms. For example, in some cases, likelihood of atelectasis may not be considered above a nominal value until aircraft cabin has reached a cabin pressure or G-force measurement outside of a certain range for a certain duration, such as without limitation cabin pressure exceeding 8,000 feet for longer than 30 minutes or cabin pressure exceeding 25,000 for any amount of time. In some cases, cabin pressure may be referred to using analogous elevation (e.g., in feet), such that lower pressures relate to higher elevations.

With continued reference to FIG. 1, computing device 104 may be configured to generate a dosing schedule 124. As used in this disclosure, a "dosing schedule" is a routine of intervention for a flight crew member that will reduce his likelihood of atelectasis. In some cases, a dosing schedule may prescribe cabin pressures not to exceed a certain cabin altitude. Alternatively or additionally, in some cases, a dosing schedule may contraindicate high G-force maneuvers, over a certain g-force threshold. In some cases, dosing schedule may prescribe durations and/or frequencies for interventions (e.g., avoiding high G-forces and low cabin pressure). In some cases, computing device 104 may be configured to generate a dosing schedule 124 as a function of likelihood of atelectasis 120. According to some embodiments, computing device 104 may determine a dosing schedule using at least a machine-learning process. Machine-learning process may include any machine-learning process, for example explained in reference to FIGS. 6-9.

Still referring to FIG. 1, in some embodiments, at least an environmental sensor 116 may additionally include an accelerometer 128. In some cases, accelerometer may be a constituent of an inertial measurement unit (IMU). In some cases, accelerometer 128 may be configured to measure a G-force affecting flight crew member. As used in this disclosure, "G-force" is an abbreviation for gravitational force equivalent, which is a measurement of force per unit mass (i.e., acceleration) that causes a perception of weight. Typically, 1 G of G-force may be equal to gravitational acceleration on Earth, g, or about 9.8 m/s$^2$. In some cases, computing device 104 may be further configured to determine likelihood of atelectasis 120 as a function of G-force. For instance, in some cases, determining likelihood of atelectasis 120 may include comparing measured G-force with a G-force threshold. As used in this disclosure, a "G-force threshold" is a certain G-force value. In some cases, G-force threshold may be predetermined. In some cases, G-force threshold may be determined, using computing device, as a function of detected parameters or likelihood of atelectasis, and may change over time. In some cases, G-force threshold may be compared to measured G-force, using computing device.

Still referring to FIG. 1, in some embodiments, computing device 104 may be further configured to determine a recompression schedule 132 for flight crew member. In some cases, computing device 104 may be further configured to determine a recompression schedule 132 as a function of likelihood of atelectasis 120. As used in this disclosure, a "recompression schedule" is a course prescribing environmental pressure and time. In some cases, a recompression schedule 132 may intend to reduce a flight crew members likelihood of atelectasis. In some cases, a recompression schedule 132 may reverse atelectasis. In some embodiments, computing device 104 may determine a recompression schedule using at least a machine-learning process. Machine-learning process may include any machine-learning process, for example explained in reference to FIGS. 6-9.

Still referring to FIG. 1, in some embodiments, system 100 may additionally include a user interface 136 in communication with computing device 104. In some cases, user interface 136 may be configured to communicate an alert, for instance to flight crew member or another user. In some cases, user interface 136 may be configured to communicate alert as a function of likelihood of atelectasis 120. As used in this disclosure, an "alert" is a communication to a flight crew member. In some cases, an alert may indicate a warning pertaining to a flight crew member's risk of atelectasis. An alert may be communicated audibly, visually, and/or haptically. In some cases, alert may include a message. In some cases, message may be configured to communicate at least a portion of one or more of dosing schedule 124 and recompression schedule 132. As used in this disclosure, a "message" is a communication configured to communicate information. For example, in some cases, a message may communicate a dosing schedule. Alternatively or additionally, a message may communicate a recompression schedule. A message may be communicated visually, audibly, and/or haptically. As used in this disclosure, a "user interface" is a system that is designed and/or configured to facilitate communication between at least a system, such as without limitation a processor, and a user by way of at least an output communicated to the user and/or at least an input communicated from the user. Exemplary non-limiting user interfaces 136 include displays, audio systems, haptic systems, head mounted displays, mice, joysticks, keyboards, and the like. User interface 136 may be configured to alert flight crew member as a function of likelihood of atelectasis. In some cases, user interface 136 may include headphones, for example over ear headphones including an earcup. In some cases, user interface may include a bone conducting transducer, for example located within an earcup of a headphone. A "bone-conducting transducer," as used in this disclosure, is a device or component that converts an electric signal to a vibrational signal that travels through bone in contact with the device or component to an inner ear of user, which interprets the vibration as an audible signal. Bone-conducting transducer may include, for instance, a piezoelectric element, which may be similar to the piezoelectric element found in speakers or headphones, which converts an electric signal into vibrations. In an embodiment, bone-conducting transducer may be mounted to housing in a position placing it in contact with a user's bone; for instance, where housing includes or is incorporated in an ear cup, housing may place bone-conducting transducer in contact with user's skull just behind the ear, over the sternocleidomastoid muscle. Likewise, where housing includes a headset, mask, or helmet, housing may place bone-conducting transducer in contact with a portion of user's skull that is adjacent to or covered by headset, mask, or helmet. Additional disclosure related to headphones and bone conducting transducers may be found in U.S. patent application Ser. No. 16/859,483 filed on Apr. 27, 2020, entitled "HUMAN PERFORMANCE OXYGEN SENSOR," the entirety of which is incorporated herein by reference.

Still referring to FIG. 1, in some embodiments, at least a user interface 136 may include an audio system. As used in this disclosure, an "audio system" is a system that is configured to transduce a signal to sound and/or vice versa. Non-limiting exemplary audio systems include loudspeakers, headphones, microphones, bone-conducting transducers, and the like. In some cases, at least a user interface 136 may be configured to generate auditory coaching to user, for instance as a function of one or more of likelihood of atelectasis 120, dosing schedule 124, and recompression schedule 132. As used in this disclosure, "auditory coaching" is audio instructions intended for a user to listen and respond to. Auditory coaching may be selected based upon likelihood of atelectasis 120. For example, different auditory coaching may be selected depending upon value of likelihood of atelectasis. Auditory coaching may include any instructions to avoid or recover from atelectasis described in this disclosure, including those described in detail below.

With continued reference to FIG. 1, in some embodiments, computing device 104 may perform one or more of determining likelihood of atelectasis 120, generating dosing schedule 124, and generating recompression schedule 132 by way of one or more algorithms. Exemplary algorithms are provided below in greater detail. In some cases, computing device 104 may be configured to operate multiple algorithms, some or all of these algorithms may be user selected and/or adjusted. In some cases, one or more particular algorithms may be selected, for example by way of user interface 136. In some cases, one or more settings associated with algorithms may, likewise, be selected, for example by way of user interface 136. Exemplary non-limiting settings may include thresholds, time-delays, debounces, and the like. In some cases, authentication may be required prior to adjusting settings.

With continued reference to FIG. 1, in some cases, computing device 104 may be configured to perform a threshold algorithm. For example, in some cases, computing device 104 may compare one or more parameters to at least a preset threshold and/or at least a preset range. In some exemplary embodiments, a value representing one or more of at least an exhalation parameter, at least an inhalation parameter, and/or at least an environmental parameter is found to be outside of at least a preset range for at least a predetermined period of time, computing device 104 may detect a condition affecting atelectasis. In some embodiments, computing device 104 may use a plurality of preset thresholds and/or preset ranges. For example in some cases a first threshold may be used to indicate a potential presence or future presence of a condition and a second threshold may be used to indicate a high likelihood of atelectasis.

With continued reference to FIG. 1, in some cases, computing device 104 may be configured to compare parameter values against a baseline. For example, in some cases, a preset threshold and/or preset range may be determined by computing device 104 according to historical data (e.g., baseline), for example historical data related to flight crew member.

Figure 2:
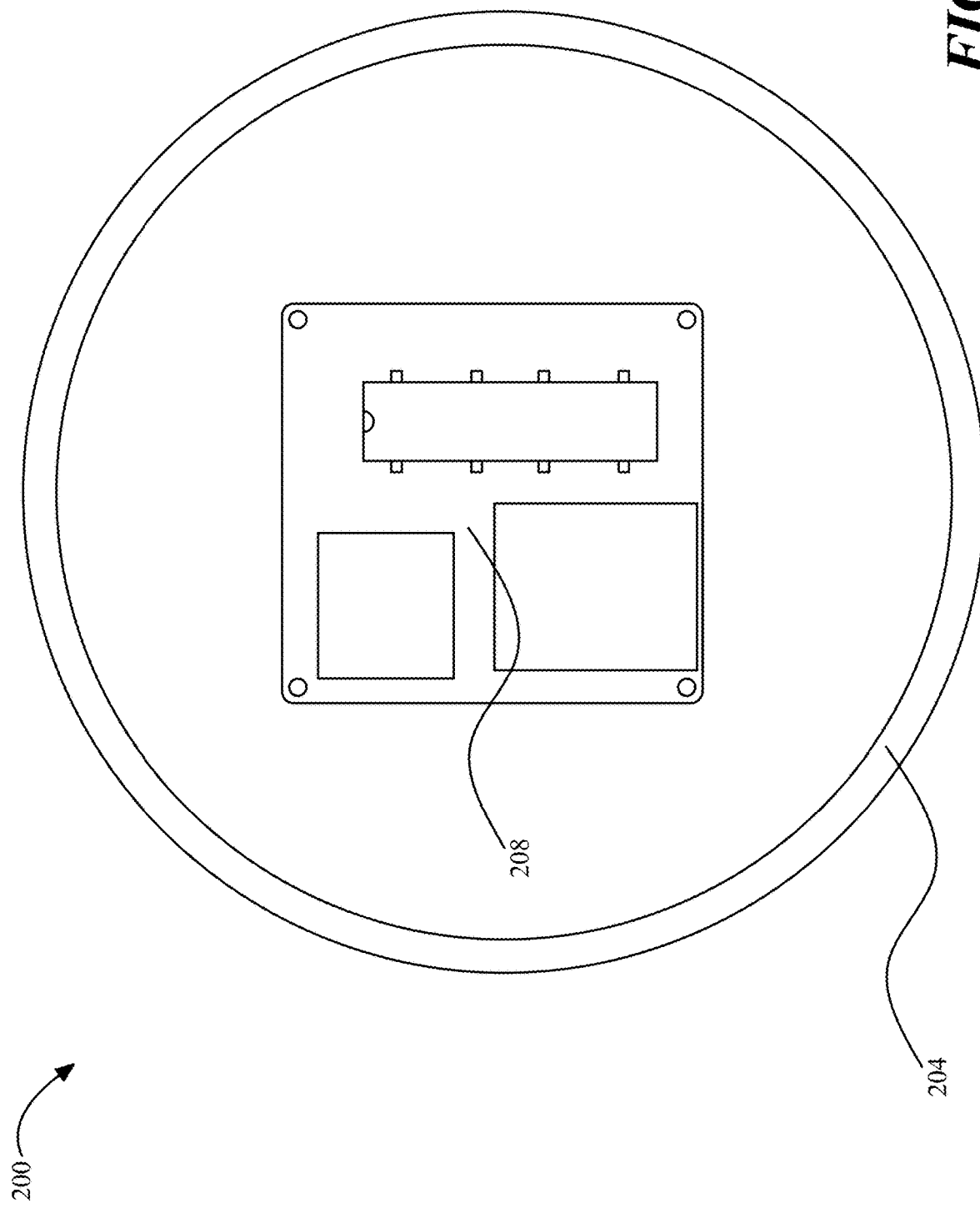
FIG. 2 illustrates an exemplary combination exhalation and environmental gas sensor.

Referring now to FIG. 2, a combined exhalation and environmental gas sensor 208 apparatus 200 for mobile respiratory equipment is illustrated. Apparatus 200 includes a housing 204, within which one or more electronic components are positioned. One or more electric components include a sensor 208. Housing 204 may be constructed of any suitable material or combination of materials, including without limitation metal, metal such as aluminum, titanium, steel, or the like, plant materials including bamboo and/or wood, polymer materials such as polycarbonate, polymethyl methacrylate, acrylonitrile butadiene styrene (ABS), or the like, synthetic fibers such as carbon fiber, silicon carbide fiber, metallic fiber, or the like, composite materials such as fiberglass, laminated fiberglass, plywood, or the like, or any combination of the above. Housing 204 may be manufactured in any suitable process including molding such as injection molding, additive manufacturing such as "three-dimensional printing" and/or stereolithography, subtractive processes such as machining, and/or any other process or combination of processes. Housing 204 may include a sensor-bearing surface 212 on or to which one or more electrical components including sensor 208 may be attached. Sensor-bearing surface 212 may be positioned opposite a port aperture as described in further detail below.

Figure 3B:
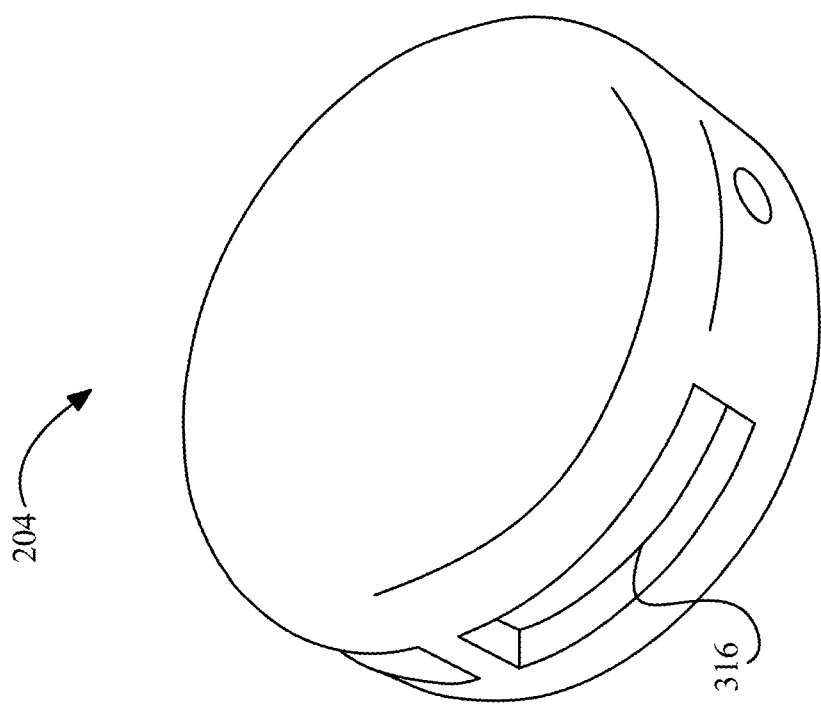
FIG. 3B is a second view of an exemplary combination exhalation and environmental gas sensor.
Figure 3A:
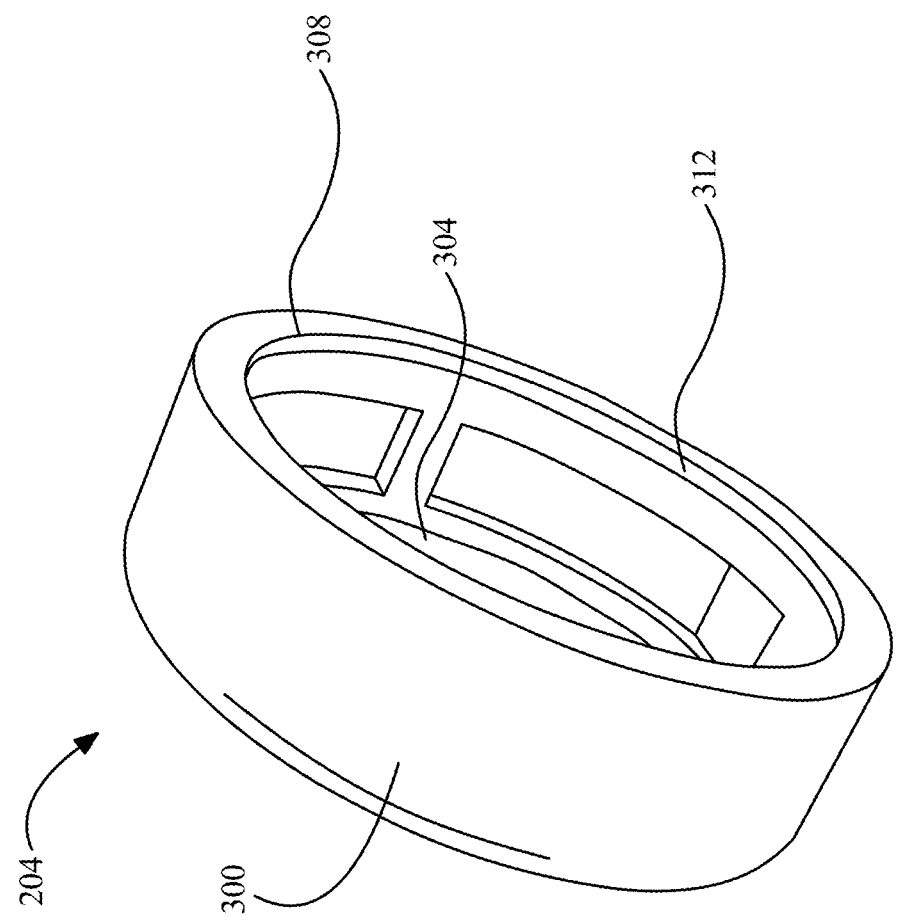
FIG. 3A is a first view of an exemplary combination exhalation and environmental gas sensor.

Referring now to FIG. 3A, a perspective view of an exemplary embodiment of a housing 204 is illustrated. Housing 204 may include an exterior surface 300, an interior surface 304, an interior space surrounded by interior surface 304, and one or more apertures. Housing 204 may have any suitable shape, including a shape of a cap to be placed over a respiratory exhaust port as described in further detail below. Housing 204 may be substantially cylindrical and may have one or more rounded edges. Housing 204 includes a port aperture 308. Port aperture 308 is an aperture that receives exhaled breath from a respiratory exhaust port as described in further detail below, admitting the exhaled breath into interior space of housing 204. Housing 204 further includes a connector 312, which may be located at port aperture 308. A "connector," as used in this disclosure, is a structural feature and/or component that affixes one aperture, opening, port, or the like to another in a way that permits flow of fluids such as liquid and/or gases to flow from one aperture, opening, port, or the like to another. Connector 312 is configured to attach port aperture 508 to exhaust port. Connector 312 may include, without limitation, a rim that fits and/or snaps over a feature of exhaust port to affix port aperture 308 thereto; connector 312 may alternatively or additionally include fastener, such as a bold or screw that inserts through a hole in housing 204 and screws into a reciprocally threaded hole in exhaust port. Connector 312 may include threading around port aperture 308 that engages reciprocal threading at exhaust port. Connector 312 may include and/or be combined with adhesives, sealants, or the like. Connector 312 may permit repeated detachment and reattachment or may effect a permanent connection between port aperture 308 and exhaust port. Persons skilled in the art, upon reviewing the entirety of this disclosure, will be aware of various alternative or additional structures and/or components that may be used for connector 312. Port aperture 308 may be located opposite sensor-bearing surface 312; for instance, sensor-bearing surface 312 may be located on interior surface 304 at a distal end of housing 204, while port aperture 308 may be located at a proximal end of housing 204.

Referring now to FIG. 3B, housing 204 includes at least an ambient aperture 316 connecting to an exterior environment. An "exterior environment," as used in this disclosure, means air that is exterior to an element of mobile respiratory equipment as described below; for instance, where mobile respiratory equipment is a respirator mask, exterior environment may include air outside of the mask and around a person wearing the mask, as opposed to air or gas between the mask and mouth or nose of the person. At least an ambient aperture 316 includes an opening connecting interior space to exterior environment. At least an ambient aperture 316 may permit air to travel freely between interior space and exterior environment.

Figure 4:
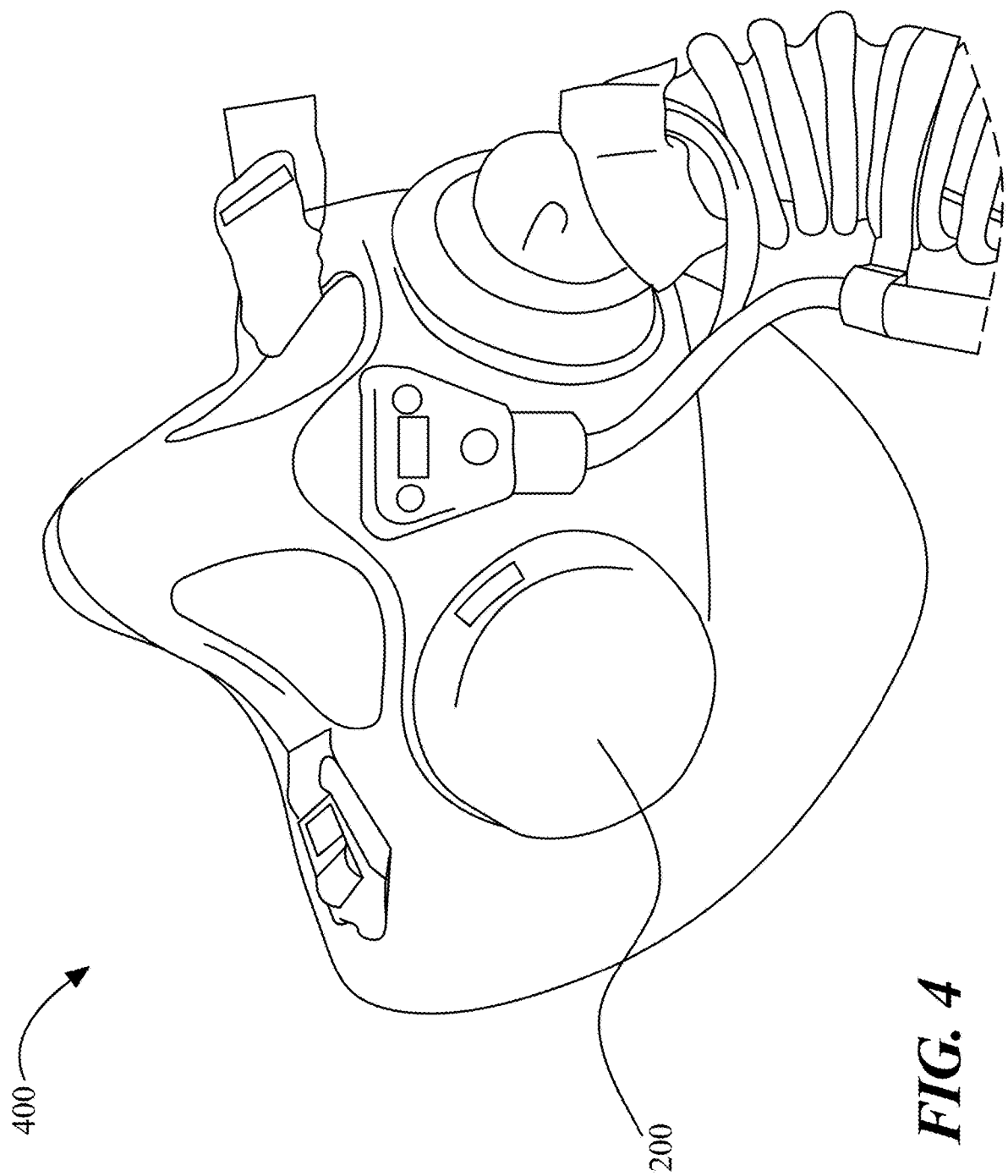
FIG. 4 illustrates an exemplary exhalation and environmental gas sensor on a face mask.

In an embodiment, and referring now to FIG. 4, housing 204 may be attached to an exhaust port of a mobile respiratory device 400. A "mobile respiratory device," as used herein, is a device worn on or about a face of a person, which aids in respiration, for instance when the person is in an environment where oxygen may be scarce or where other gases or particular matter such as carbon dioxide, carbon dioxide, toxic gases, droplets or fumes, or other elements that may interfere with respiration, and/or gases having ambient temperatures capable of harming a person when inhaled. Such an environment may include, without limitation, a cockpit of an aircraft such as a military aircraft, an artificially or naturally formed tunnel with an atmosphere that makes breathing difficult, such as an anoxic atmosphere, an atmosphere containing poisonous or otherwise problematic gases such as sulfur dioxide, carbon dioxide, carbon monoxide, or the like, a location at a high altitude such as a mountaintop, a location of a chemical spill and/or the like.

Still referring to FIG. 4, mobile respiratory device 400 may include, without limitation, a gas mask such as a cannister mask, a self-contained breathing apparatuses (SCBA) such as those used by firefighters, self-contained underwater breathing apparatuses (SCUBA), supplied-air respirators (SAR), particulate respirators, chemical cartridge respirators, powered air-purifying respirators (PAPRs), respirators included as part of a protective suit, airline respirators, N-95 or other NIOSH approved respirators, and/or other devices worn on and/or over and at least partially occluding the face to aid in respiration.

With continued reference to FIG. 4, an "exhaust port," as used in this disclosure, is an outlet that permits air exhaled by a user to escape from a mobile respiratory device 400. Exhaust port may include a valve such as a check-valve or other one-way valve to prevent air from entering a mobile respiratory device 400 from environment. Exhaust port may include, for instance, an exhale valve of a respirator mask or other such design. Exhaust port may also be an inlet port; for instance, air may be filtered while breathing in through the port and then exhaled, with or without filtering, via a valve at the same port. In operation, housing 204 with port aperture 308 and ambient aperture 316 may form a plenum in which exhaled and ambient air may flow freely by sensor 208, permitting sensation of both breath composition and environmental air composition. Further disclosure related to combined exhaled gas and environmental gas sensor may be found in U.S. patent application Ser. No. 16/933,680, entitled "COMBINED EXHALED AIR AND ENVIRONMENTAL GAS SENSOR APPARATUS," the entirety of which is incorporated herein by reference.

Figure 5:
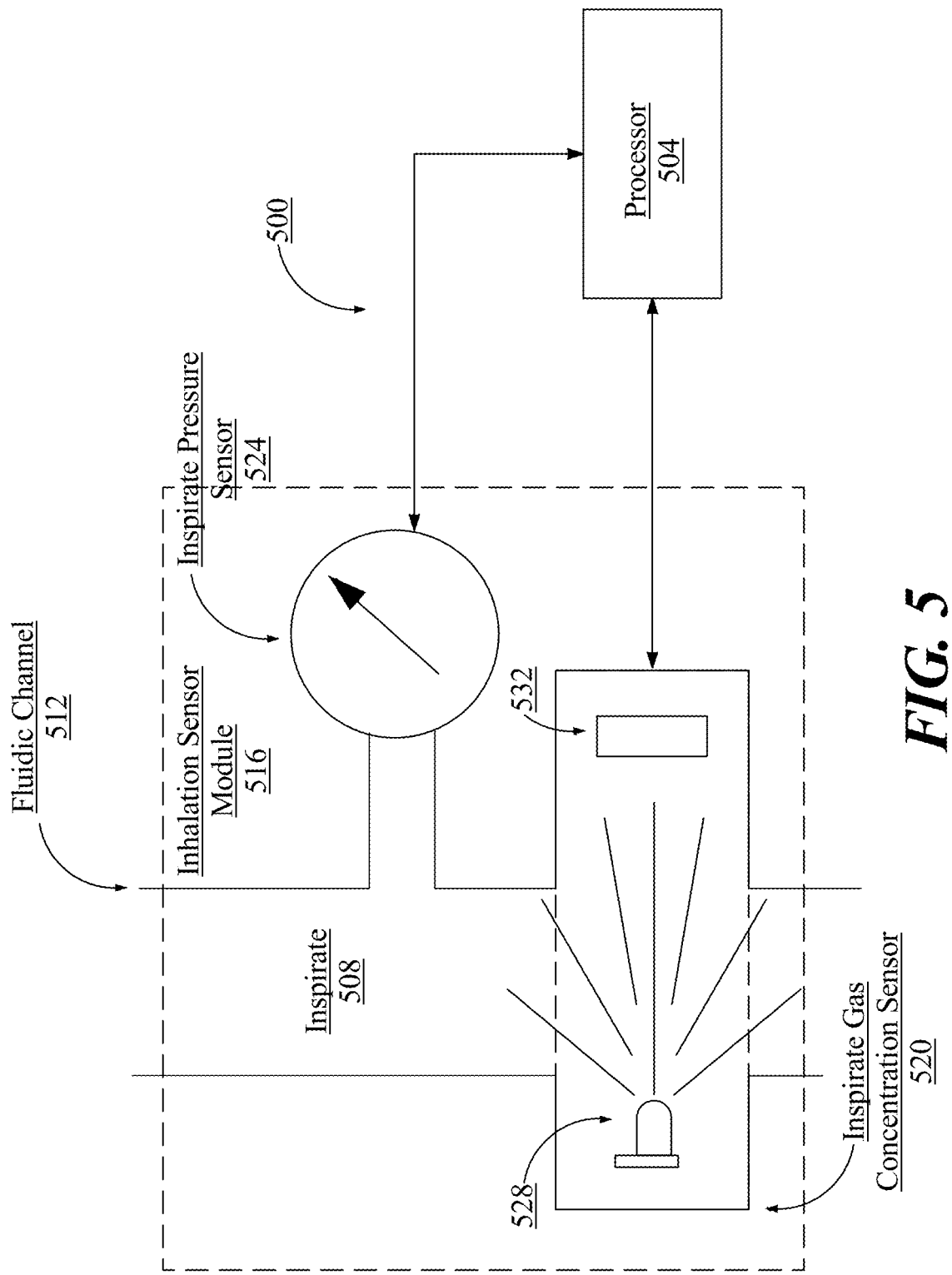
FIG. 5 is a block diagram of an exemplary inhalation sensor.

Referring now to FIG. 5, an exemplary inhalation sensor 500 is illustrated. In some embodiments, inhalation sensor 500 may include a processor 504 for making determinations as a function of sensed parameters associated with at least an inspirate 508. in communication with an exemplary inhalation sensor module 508. In some cases, at least a portion of an at least an inspirate 508 is contained within a fluidic channel 512. An exemplary inhalation sensor module 516 is shown in fluid communication with fluidic channel 512. In some cases, inhalation sensor module may include at least a gas concentration sensor 520. In some cases, inhalation sensor module 516 may include at least an inspirate pressure sensor 524. Inspirate gas concentration sensor 520 may include any gas concentration sensor, for instance those described in this application. In some cases, inspirate gas concentration sensor 520 may include an optical gas concentration sensor. Non-limiting optical gas concentration sensors include infrared transmission and/or absorbance spectroscopy type sensors and fluorescence excitation type sensors. Commonly, an optical gas concentration sensor may include a radiation source 528 and a radiation detector 532. In some versions, radiation source 528 may include a light source 528 that may generate a light and illuminate at least a portion of at least an inspirate 508. Radiation source 528 may generate any of a non-limiting list of lights, including coherent light, non-coherent light, narrowband light, broadband light, pulsed light, continuous wave light, pseudo continuous wave light, ultraviolet light, visible light, and infrared light. In some cases, radiation source 528 may include an electromagnetic radiation source that may generate an electromagnetic radiation and irradiate at least a portion of at least an inspirate 508. Radiation source 528 may generate any of a non-limiting list of radiations including radio waves, microwaves, infrared radiation, optical radiation, ultraviolet radiation, X-rays, gamma-rays, and light. Non-limiting examples of radiation sources 528 include lasers, light emitting diodes (LEDs), light emitting capacitors (LECs), flash lamps, antennas, and the like. In some cases, radiation detector 532 may be configured to detect light and/or radiation that has interacted directly or indirectly with at least a portion of at least an inspirate 508.

Non-limiting examples of radiation detectors 532 include photodiodes, photodetectors, thermopiles, pyrolytic detectors, antennas, and the like. In some cases, a radiation amount detected by radiation detector 532 may be indicative of a concentration of a particular gas in at least a portion of at least an inspirate 508. For example, in some exemplary embodiments, radiation source 528 may include an infrared light source operating at a wavelength about 4.6 µm and radiation detector may include a photodiode sensitive over a range encompassing 4.6 µm. An exemplary infrared light source may include an LED comprising InAsSb/InAsSbP heterostructures, for example LED46 from Independent Business Scientific Group (IBSG) of Saint Petersburg, Russia. An exemplary infrared detector may include a mercury cadmium telluride photodiode, for example UM-I-6 HgCdTe from Boston Electronics of Brookline, Massachusetts. In some cases, an amount of radiation at least a specific wavelength absorbed, scatter, attenuated, and/or transmitted may be indicative of a gas concentration.

With continued reference to FIG. 5, in some cases, inspirate concentration sensor 520 may include an infrared point sensor. An infrared (IR) point sensor may use radiation passing through a known volume of gas, for example at least an inspirate 508. In some cases, detector 532 may be configured to detect radiation after passing through gas at a specific spectrum. As energy from infrared may be absorbed at certain wavelengths, depending on properties of at least an inspirate 520. For example, carbon monoxide absorbs wavelengths of about 4.2-4.5 µm. In some cases, detected radiation within a wavelength range (e.g., absorption range) may be compared to a wavelength outside of the wavelength range. A difference in detected radiation between these two wavelength ranges may be found to be proportional to a concentration of gas present. In some embodiments, an infrared image sensors may be used for active and/or passive imaging. For active sensing, radiation source 528 may include a coherent light source (e.g., laser) which may be scanned across a field of view of a scene and radiation detector 532 may be configured to detect backscattered light at an absorption wavelength of a specific target gas. In some cases, radiation detector 532 may include an image sensor, for example a two-dimensional array of radiation sensitive devices, for example arranged as pixels. Passive IR imaging sensors may measure spectral changes at each pixel in an image and look for specific spectral signatures that indicate presence and/or concentration of target gases.

With continued reference to FIG. 5, in some cases, inspirate gas concentration sensor 520 may include an oxygen sensor. An exemplary oxygen sensor may include an electro-galvanic sensor. For example, an electro-galvanic oxygen sensor may be used to measure a concentration of oxygen within at least an inspirate 508. In some cases, an electro-galvanic oxygen sensor may include a lead/oxygen galvanic cell, within which oxygen molecules are dissociated and reduced to hydroxyl ions at a cathode. Hydroxyl ions may diffuse through an electrolyte and oxidize a lead anode. A current proportional to a rate of oxygen consumption may be generated when cathode and anode are electrically connected through a resistor. Current may be sensed by known current sensing methods, for example without limitation those described in this disclosure, to produce an electrical signal proportional to a concentration of oxygen, for example oxygen within at least an inspirate. Another exemplary oxygen sensor may include a lambda sensor, for example a zirconia sensor, a wideband zirconia sensor and/or a titania sensor. A lambda sensor may be configured to sense a quantity of oxygen in a gas (e.g., at least an inspirate 508) relative another gas, for example air within an environment (e.g., cabin air) and transmit an analog voltage correlated to the sensed relative quantity of oxygen. Analog voltage transmitted by a lambda sensor may be processed by any data or signal processing methods discussed herein, for example through amplification and/or analog-to-digital conversion.

In another exemplary embodiment, inspirate concentration sensor 520 may include an optical sensor configured to sense oxygen concentration. In some cases, a chemical film is configured to be in contact with a gas (e.g., at least an inspirate 508). Chemical film may have fluorescence properties which are dependent upon presence and/or concentration of oxygen. Radiation detector 532 may be positioned and configured, such that it is in sensed communication with chemical film. Radiation source 528 may irradiate and/or illuminate chemical film with radiation and/or light having properties (e.g., wavelength, energy, pulse duration, and the like) consistent with exciting fluorescence within the chemical film. In some cases, fluorescence may be at a maximum when there is no oxygen present. For example, oxygen molecules may collide with chemical film and quench photoluminescence resulting from fluorescent excitation. A number of O2 molecules colliding with chemical film may be correlated with a concentration of oxygen within a gas (e.g., inspirate 508). Fluorescence properties as sensed by optical detector 532 may therefore be related to oxygen concentration. Fluorescence properties may include emission duration, fluorescence energy, and the like. In some cases, detected optical signal (fluorescence) to oxygen concentration may not be linear. For instance, an optical oxygen sensor may be most sensitive at low oxygen concentration; that is, sensitivity decreases as oxygen concentration increases, following a known Stern—Volmer relationship. In some cases, an optical oxygen sensor is advantageous as substantially no oxygen may be consumed, during sensing. In some cases, planar optical oxygen sensors (i.e., optodes) may be used to detect a spatial distribution of oxygen concentrations over an area, for example as a two-dimensional image. Based on the same principle, radiation detector 532 may include a digital camera that may be used to capture fluorescence intensities over a specific area.

With continued reference to FIG. 5, inhalation sensor module 516 may include at least an inspirate pressure sensor 524, which is fluidic communication with at least an inspirate 508, for example by way of at least a fluidic channel 512. In some cases, at least an inspirate pressure sensor 516 may be configured to sense and transmit at least an inspirate pressure parameter as a function of a pressure of at least an inspirate 508. In some cases, inhalation pressure sensor 524 may include any type of pressure sensor described in this disclosure. Inhalation pressure sensor 524 may be a force collector type pressure sensor. Alternatively, in some case, inhalation pressure sensor 524 may be a pressure sensor type that does not use force collection. Further disclosure related to inhalation sensor may be found in U.S. patent application Ser. No. 17/333,169, entitled "SYSTEMS AND METHODS FOR INSPIRATE SENSING TO DETERMINE A PROBABILITY OF AN EMERGENT PHYSIOLOGICAL STATE," the entirety of which is incorporated herein by reference.

Figure 6:
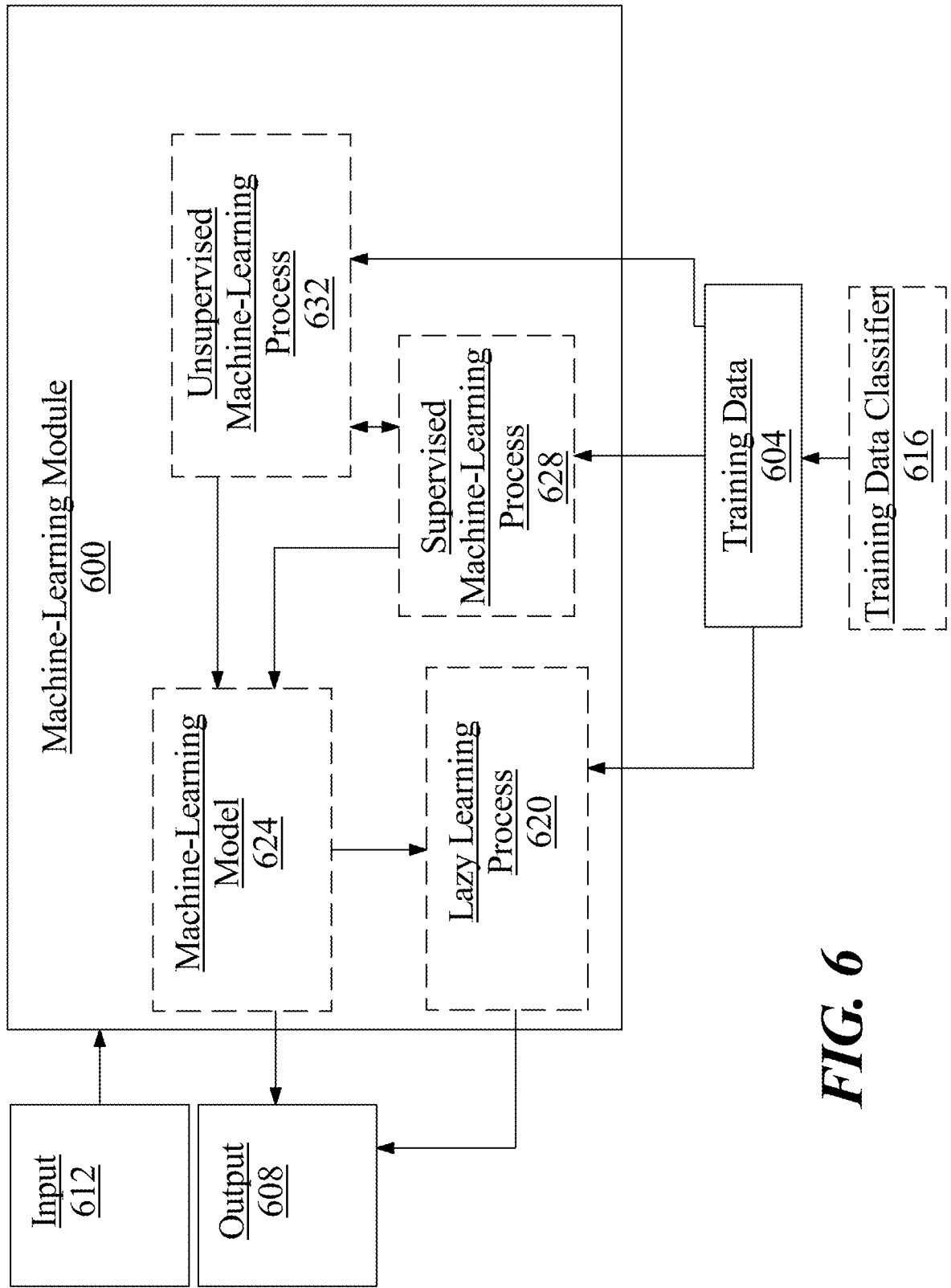
FIG. 6 illustrates a block diagram of an exemplary machine-learning process.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure. In some cases, training data may be configured to train a machine-learning process to aid in determination of likelihood of atelectasis 120. For example training data may include historic or deterministic values for one or more of at least an exhalation parameter, at least an inhalation parameter, and/or at least an environmental parameter, as inputs correlated with outputs representing a known value representing atelectasis, such as without limitation presence of atelectasis (e.g., Boolean value), severity of atelectasis (e.g., on an arbitrary scale [1-10]), and/or likelihood of atelectasis (e.g., on an arbitrary scale [1-10]).

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to a specific flight crew member or cohort of flight crew members. As a non-limiting illustrative example one or more of at least an exhalation parameter, at least an inhalation parameter, and/or at least an environmental parameter may be categorized according to user (i.e., flight crew member) and/or user cohort. In some cases, a machine-learning model may need to be trained using training substantially from only one user (i.e., flight crew member). Alternatively or additionally, in some cases, training data may include one or more of at least an exhalation parameter, at least an inhalation parameter, and/or at least an environmental parameter from a population of users.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 7:
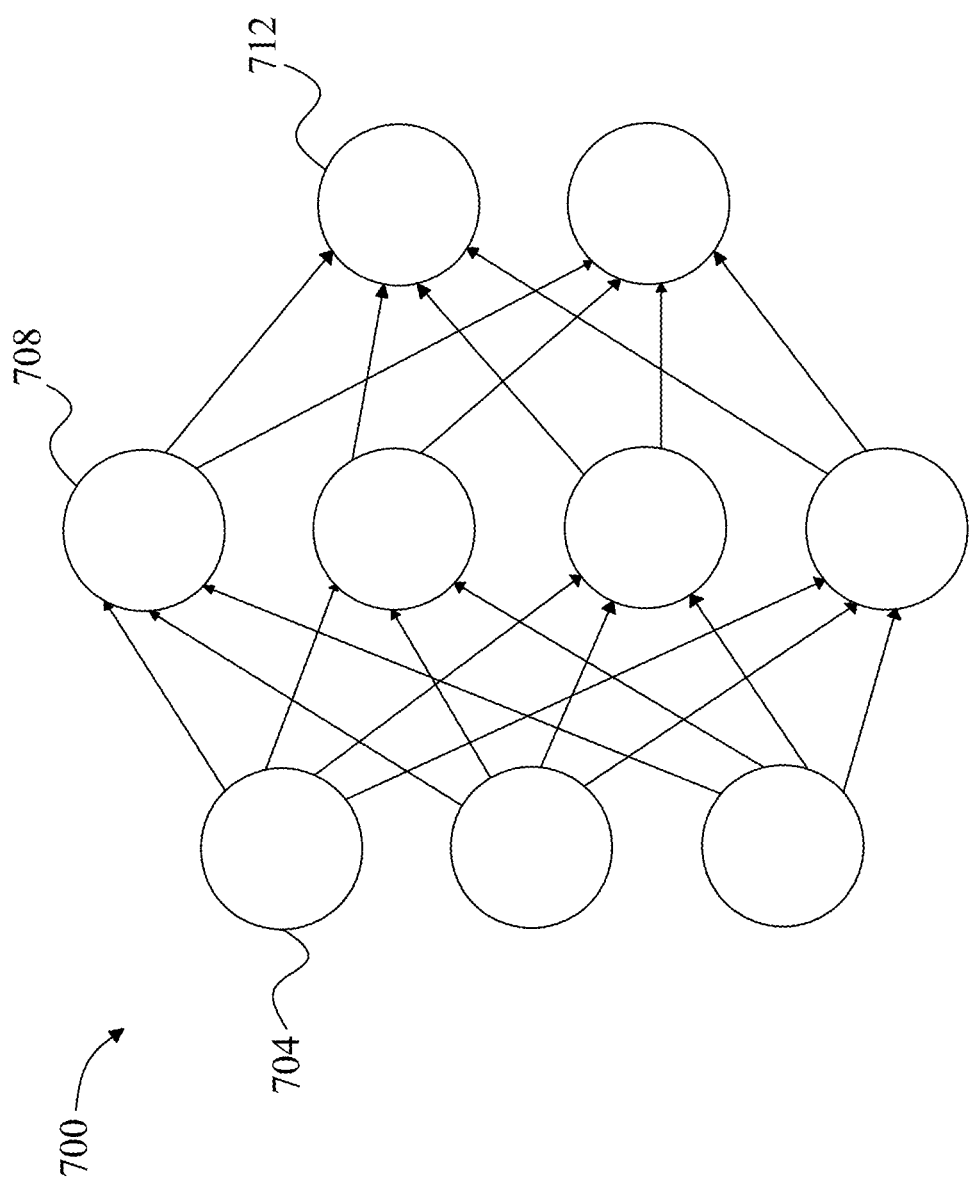
FIG. 7 illustrates an exemplary neural network.

Referring now to FIG. 7 an exemplary embodiment of neural network 700 is illustrated. Neural network also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 704, one or more intermediate layers 708, and an output layer of nodes 712. Connections between nodes may be created via the process of "training" the network, in which elements from a training dataset are applied to input nodes 704, a suitable training algorithm (such as Levenberg-Marquardt, conjugate gradient, simulated annealing, or other algorithms) is then used to adjust the connections and weights between nodes in adjacent layers 708 of the neural network to produce the desired values at output nodes 712. This process is sometimes referred to as deep learning.

Figure 8:
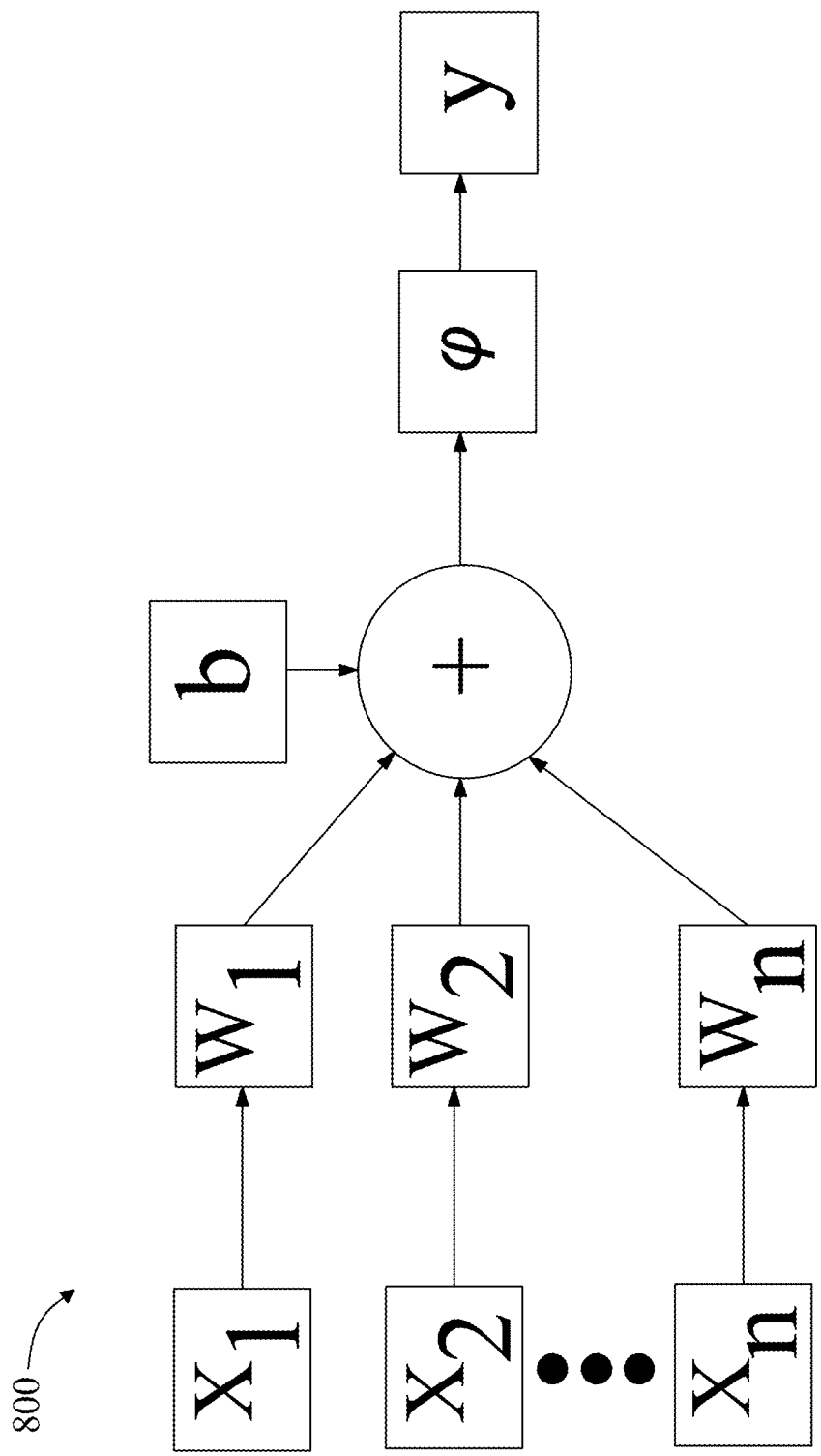
FIG. 8 illustrates an exemplary node of a neural network.

Referring now to FIG. 8, an exemplary embodiment of a node 800 of a neural network is illustrated. A node 800 may include, without limitation a plurality of inputs $x_i$ that may receive numerical values from inputs to a neural network containing the node and/or from other nodes. Node 800 may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 8, a neural network may receive one or more of at least an exhalation parameter, at least an inhalation parameter, and/or at least an environmental parameter, as inputs and output one or more of a likelihood of atelectasis 120, a dosing schedule 124 and/or a recompression schedule 132. Alternatively or additionally in some cases, a neural network may receive one or more of at least an exhalation parameter, at least an inhalation parameter, and/or at least an environmental parameter as inputs and output a confidence metric representing a probability of classification to a predetermined class, for instance likelihood of atelectasis 120, dosing schedule 124, and/or recompression schedule 132, according to weights $w_i$ that are derived using machine-learning processes as described in this disclosure.

Referring again to FIG. 1, In some embodiments, computing device 104 may be configured to modify a training set in response to one or more of at least an exhalation parameter, at least an inhalation parameter, and/or at least an correlated to a likelihood of atelectasis 120, dosing schedule 124, and/or recompression schedule 132; where likelihood of atelectasis 120, dosing schedule 124, and/or recompression schedule 132 may represent an actual known occurrence that is related to a user (i.e., flight crew member). For example, computing device 104 may, in some cases, retrain a machine-learning model using one or more of at least an exhalation parameter, at least an inhalation parameter, and/or at least an environmental parameter correlated to likelihood of atelectasis 120, dosing schedule 124, and/or recompression schedule 132. In some embodiments, computing device 104 may be configured to classify at least one of a likelihood of atelectasis 120, dosing schedule 124, and/or recompression schedule 132 and determine a confidence metric. For example, in some exemplary embodiments confidence metric may be a floating-point number within a prescribed range, such as without limitation 0 to 1, with each end of the prescribed range representing an extreme representation, such as without limitation substantially no confidence and substantially absolute confidence, respectively. In some cases, confidence output may represent a relationship between a result of filtering and/or classifying. Confidence metric may be determined by one more comparisons algorithms, such as without limitation a fuzzy set comparison. For example, in some exemplary embodiments a fuzzy set comparison may be employed to compare a probabilistic outcome, such as without limitation likelihood of atelectasis 120, with a membership function derived to represent at least a threshold used for classification.

Figure 9:
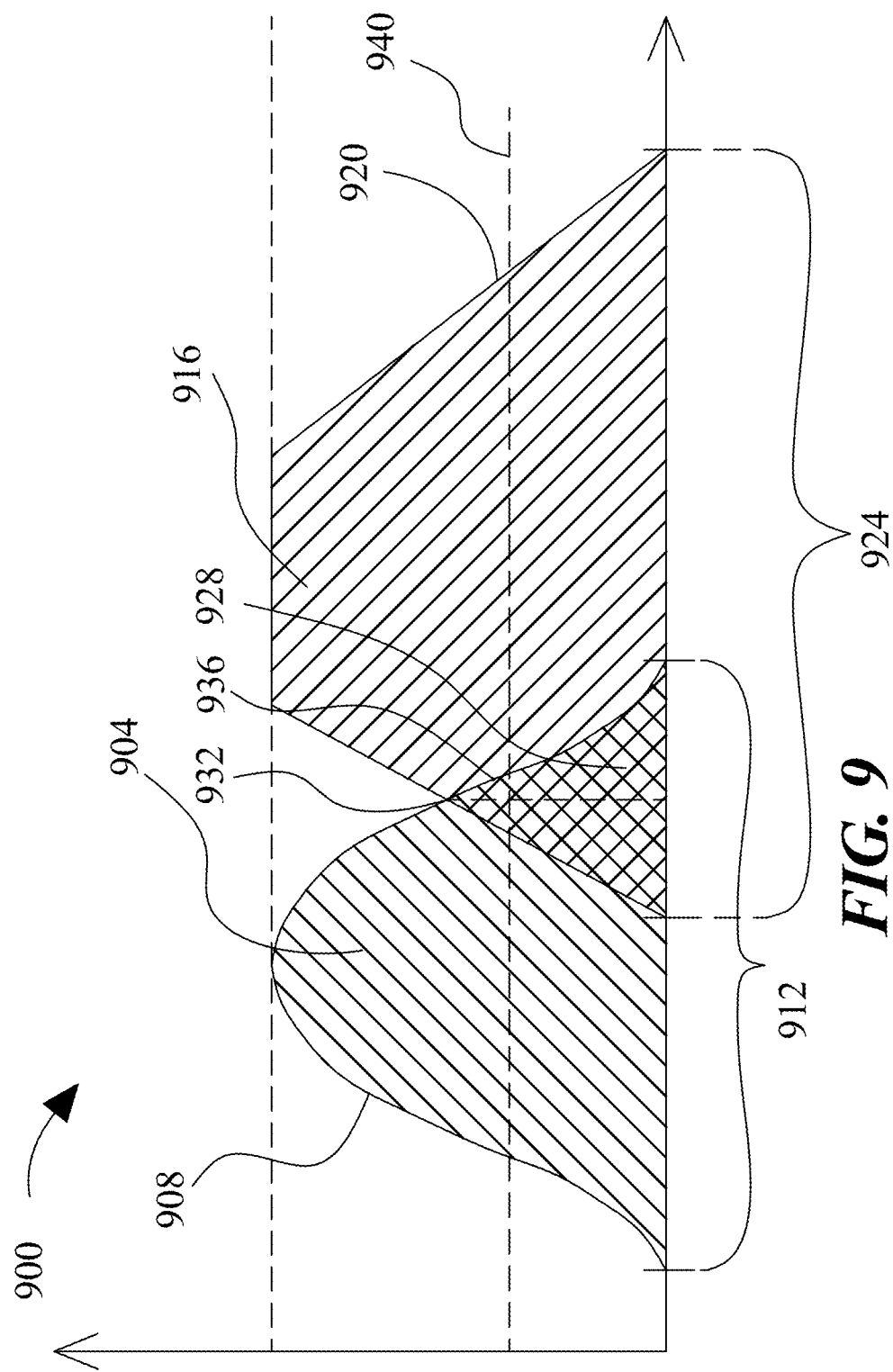
FIG. 9 graphically depicts comparison of two exemplary fuzzy logic sets.

Referring to FIG. 9, an exemplary embodiment of fuzzy set comparison 900 is illustrated. A first fuzzy set 904 may be represented, without limitation, according to a first membership function 908 representing a probability that an input falling on a first range of values 912 is a member of the first fuzzy set 904, where the first membership function 908 has values on a range of probabilities such as without limitation the interval [0,1], and an area beneath the first membership function 908 may represent a set of values within first fuzzy set 904. Although first range of values 912 is illustrated for clarity in this exemplary depiction as a range on a single number line or axis, first range of values 912 may be defined on two or more dimensions, representing, for instance, a Cartesian product between a plurality of ranges, curves, axes, spaces, dimensions, or the like. First membership function 908 may include any suitable function mapping first range 912 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 9, first fuzzy set 904 may represent any value or combination of values as described above, including output from one or more algorithms, one or more machine-learning models and one or more of at least an exhalation parameter, at least an inhalation parameter, and/or at least an environmental parameter, a likelihood of atelectasis 120, a predetermined class, such as without limitation a dosing schedule 124 and/or a recompression schedule 128. A second fuzzy set 916, which may represent any value which may be represented by first fuzzy set 904, may be defined by a second membership function 920 on a second range 924; second range 924 may be identical and/or overlap with first range 912 and/or may be combined with first range via Cartesian product or the like to generate a mapping permitting evaluation overlap of first fuzzy set 904 and second fuzzy set 916. Where first fuzzy set 904 and second fuzzy set 916 have a region 928 that overlaps, first membership function 908 and second membership function 920 may intersect at a point 932 representing a probability, as defined on probability interval, of a match between first fuzzy set 904 and second fuzzy set 916. Alternatively or additionally, a single value of first and/or second fuzzy set may be located at a locus 936 on first range 912 and/or second range 924, where a probability of membership may be taken by evaluation of first membership function 908 and/or second membership function 920 at that range point. A probability at 928 and/or 932 may be compared to a threshold 940 to determine whether a positive match is indicated. Threshold 940 may, in a non-limiting example, represent a degree of match between first fuzzy set 904 and second fuzzy set 916, and/or single values therein with each other or with either set, which is sufficient for purposes of the matching process; for instance, threshold may indicate a sufficient degree of overlap between an output from one or more machine-learning models (e.g., likelihood of atelectasis) and/or detected parameter and a predetermined class, such as without limitation a dosing schedule 124, for combination to occur as described above. Alternatively or additionally, each threshold may be tuned by a machine-learning and/or statistical process, for instance and without limitation as described in further detail above.

Further referring to FIG. 9, in an embodiment, a degree of match between fuzzy sets may be used to classify one or more of at least an exhalation parameter, at least an inhalation parameter, at least an environmental parameter, and/or a likelihood of atelectasis with a dosing schedule 124 and/or a recompression schedule. For instance, if likelihood of atelectasis has a fuzzy set matching a dosing schedule fuzzy set by having a degree of overlap exceeding a threshold, computing device 104 may classify the likelihood of atelectasis 120 as belonging to the dosing schedule. Where multiple fuzzy matches are performed, degrees of match for each respective fuzzy set may be computed and aggregated through, for instance, addition, averaging, or the like, to determine an overall degree of match.

Still referring to FIG. 9, in an embodiment, one or more of at least an exhalation parameter, at least an inhalation parameter, at least an environmental parameter, and/or a likelihood of atelectasis may be compared to multiple dosing schedule and/or recompression schedule fuzzy sets. For instance, likelihood of atelectasis may be represented by a fuzzy set that is compared to each of the multiple dosing schedule fuzzy sets; and a degree of overlap exceeding a threshold between the likelihood of atelectasis fuzzy set and any of the multiple dosing schedule fuzzy sets may cause computing device 104 to classify the likelihood of atelectasis as belonging to a dosing schedule. For instance, in one embodiment there may be two dosing schedule fuzzy sets, representing a moderate response to atelectasis and a minor response to atelectasis. Moderate response dosing schedule may have a moderate fuzzy set; minor response dosing schedule may have a minor fuzzy set; and likelihood of atelectasis may have a likelihood of atelectasis fuzzy set. Computing device 104, for example, may compare a likelihood of atelectasis fuzzy set with each of moderate fuzzy set and minor fuzzy set, as described above, and classify likelihood of atelectasis to either, both, or neither of moderate or mild dosing schedules. Machine-learning methods as described throughout may, in a non-limiting example, generate coefficients used in fuzzy set equations as described above, such as without limitation x, c, and ci of a Gaussian set as described above, as outputs of machine-learning methods. Likewise, one or more of at least an exhalation parameter, at least an inhalation parameter, at least an environmental parameter, and/or a likelihood of atelectasis may be used indirectly to determine a fuzzy set, as likelihood of atelectasis fuzzy set may be derived from outputs of one or more machine-learning models and/or algorithms that take the one or more of at least an exhalation parameter, at least an inhalation parameter, and/or at least an environmental parameter directly or indirectly as inputs.

Figure 10:
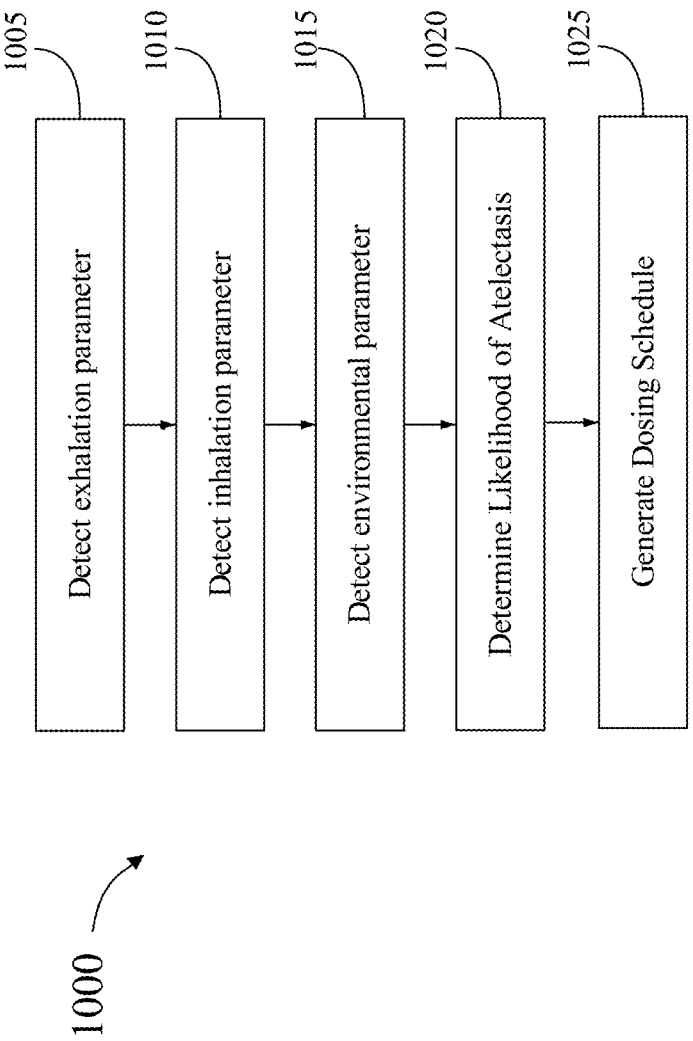
FIG. 10 is a flow diagram of an exemplary method of detecting atelectasis in flight.

Referring now to FIG. 10, a method 1000 include for detection of atelectasis in flight is illustrated by way of a flow diagram. At step 1005, method 1000 may include detecting, using at least an exhalation sensor, at least an exhalation parameter of a flight crew member. Exhalation sensor may include any exhalation sensor described in this disclosure, for example with reference to FIGS. 1-9. Exhalation parameter may include any exhalation parameter described in this disclosure, for example with reference to FIGS. 1-9. Flight crew member may include any flight crew member described in this disclosure, for example with reference to FIGS. 1-9. In some embodiments, at least an exhalation parameter may include expirate volume. Expirate volume may include any expirate volume described in this disclosure, for example with reference to FIGS. 1-9. In some embodiments, at least an exhalation parameter may include expirate carbon dioxide concentration. Expirate carbon dioxide concentration may include any carbon dioxide concentration described in this disclosure, for example with reference to FIGS. 1-10.

With continued reference to FIG. 10, at step 1010, method 100 may include detecting, using at least an inhalation sensor, at least an inhalation parameter of flight crew member. Inhalation sensor may include any inhalation described in this disclosure, for example with reference to FIGS. 1-9. Inhalation parameter may include any inhalation parameter described in this disclosure, for example with reference to FIGS. 1-9. In some embodiments, at least an inhalation parameter may include inspirate volume. Inspirate volume may include any inspirate volume described in this disclosure, for example with reference to FIGS. 1-9. In some embodiments, at least an inhalation parameter may include inspirate oxygen concentration. Inspirate oxygen concentration may include any oxygen concentration described in this disclosure, for example with reference to FIGS. 1-9.

With continued reference to FIG. 10, at step 1015, method 1000 may include detecting, using at least an environmental sensor, at least an environmental parameter of a cabin within which flight crew member may be housed. Environmental sensor may include any environmental sensor described in this disclosure, for example with reference to FIGS. 1-9. Environmental parameter may include any environmental parameter described in this disclosure, for example with reference to FIGS. 1-9.

With continued reference to FIG. 10, at step 1020, method 1000 may include determining, using a computing device, a likelihood of atelectasis for flight crew member as a function of at least an exhalation parameter, at least an inhalation parameter, and at least an environmental parameter. Computing device may include any computing device described in this disclosure, for example with reference to FIGS. 1-9 and 11. Likelihood of atelectasis may include any likelihood of atelectasis described in this disclosure, for example with reference to FIGS. 1-9. In some embodiments, determining likelihood of atelectasis may additionally include comparing detected environmental parameter with an environmental parameter threshold. Environmental parameter threshold parameter may include any environmental threshold parameter described in this disclosure, for example with reference to FIGS. 1-10.

With continued reference to FIG. 10, at step 1025, method 1000 may include generating, using computing device, a dosing schedule as a function of likelihood of atelectasis. Dosing schedule may include any dosing schedule described in this disclosure, for example with reference to FIGS. 1-9.

Still referring to FIG. 10, in some embodiments, method 1000 may additionally include measuring, using an accelerometer, G-force affecting flight crew member. In some cases, step 1020 may additionally include determining likelihood of atelectasis in part by comparing measured G-force with a G-force threshold. Accelerometer may include any accelerometer and/or motion sensor described in this disclosure, for example with reference to FIGS. 1-9. G-force may include any G-force described in this disclosure, for example with reference to FIGS. 1-9. G-force threshold may include any G-force threshold described in this disclosure, for example with reference to FIGS. 1-9.

Still referring to FIG. 10, in some embodiments, method 1000 may additionally include generating, using computing device, a recompression schedule for flight crew member as a function of the likelihood of atelectasis. Recompression schedule may include any recompression schedule described in this disclosure, for example with reference to FIGS. 1-9.

Still referring to FIG. 10, in some embodiments, method 1000 may additionally include communicating, using a user interface, an alert to flight crew member as a function of the likelihood of atelectasis. User interface may include any user interface described in this disclosure, for example with reference to FIGS. 1-9. Alert may include any alert described in this disclosure, for example with reference to FIGS. 1-9. In some cases, alert may include a message configured to communicate at least a portion of dosing schedule. Message may include any message described in this disclosure, for example with reference to FIGS. 1-9.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
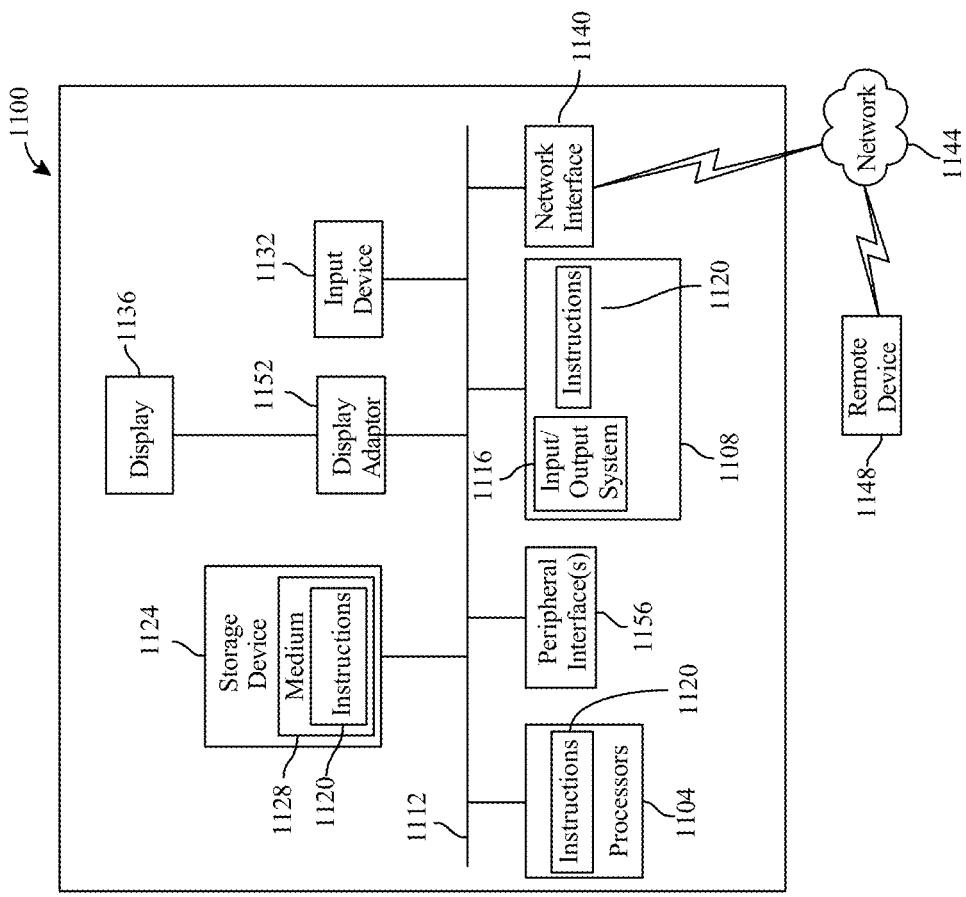
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for detection of atelectasis in flight, the system comprising:
    a mobile respiratory device comprising a mask configured to be worn on and at least partially occlude a face of a flight crew member to aid in respiration;
    at least an exhalation sensor configured to detect at least an exhalation parameter of the flight crew member;
    at least an inhalation sensor configured to detect at least an inhalation parameter of the flight crew member, wherein the at least an inhalation parameter comprises inspirate oxygen concentration, wherein the at least an inhalation sensor comprises:
        a fluidic channel, wherein the fluidic channel enables an inspirate to flow therethrough;
        an inspirate gas concentration sensor comprising:
            a chemical film comprising fluorescence properties which are dependent upon the concentration of oxygen in the inspirate;
            a radiation source that illuminates the chemical film, the radiation source comprising light properties that excite the fluorescence within the chemical film; and
            a radiation detector, wherein the radiation detector is an optical detector configured to detect the fluorescence within the chemical film; and
        a first processor, wherein the first processor is configured to determine the at least an inhalation parameter as a function of the fluorescence properties of the chemical film;
    at least an environmental sensor configured to detect at least an environmental parameter of a cabin within which the flight crew member is housed; and
    a computing device communicatively connected to the at least an exhalation sensor, the first processor of the at least an inhalation sensor, and the at least an environmental sensor, and wherein the computing device comprises:
        a memory configured to store instructions; and
        a second processor configured to perform the instructions, wherein performing the instructions comprises:
            determining a likelihood of atelectasis for the flight crew member as a function of each of the at least an exhalation parameter, the at least an inhalation parameter, and the at least an environmental parameter, wherein determining the likelihood of atelectasis comprises comparing the at least an environmental parameter to an environmental parameter threshold;
            generating a dosing schedule as a function of the likelihood of atelectasis;
            generating a recompression schedule as a function of the likelihood of atelectasis using at least a machine-learning process;
            generating an auditory coaching comprising instructions to recover from atelectasis as a function of the likelihood of atelectasis and the dosing schedule and the recompression schedule; and
            communicating the auditory coaching to the flight crew member using at least a user interface.

2. The system of claim 1, further comprising:
    an accelerometer configured to measure a G-force affecting the flight crew member; and
    wherein determining the likelihood of atelectasis comprises comparing the measured G-force with a G-force threshold.

3. The system of claim 1, further comprising using the at least a user interface configured to communicate an alert to the flight crew member as a function of the likelihood of atelectasis.

4. The system of claim 3, wherein the alert comprises a message configured to communicate at least a portion of the dosing schedule.

5. The system of claim 1, wherein the at least an exhalation parameter comprises expirate volume.

6. The system of claim 1, wherein the at least an exhalation parameter comprises expirate carbon dioxide concentration.

7. The system of claim 1, wherein the at least an inhalation parameter comprises inspirate volume.

8. A method for detection of atelectasis in flight using a mobile respiratory device including a mask to be worn on, and at least partially occluding, a face of a flight crew member to aid in respiration, the method comprising:
    detecting, using at least an exhalation sensor, at least an exhalation parameter of the flight crew member;
    detecting, using at least an inhalation sensor, at least an inhalation parameter of the flight crew member, wherein the at least an inhalation parameter comprises inspirate oxygen concentration, wherein the at least an inhalation sensor comprises:
        a fluidic channel, wherein the fluidic channel enables an inspirate to flow therethrough;
        an inspirate gas concentration sensor comprising:
            a chemical film comprising fluorescence properties which are dependent upon the concentration of oxygen in the inspirate;
            a radiation source that illuminates the chemical film, the radiation source comprising light properties that excite the fluorescence within the chemical film and
            a radiation detector, wherein the radiation detector is an optical detector configured to detect the fluorescence within the chemical film; and a first processor, wherein the first processor is configured to determine the at least an inhalation parameter as a function of the fluorescence properties of the chemical film;

detecting, using at least an environmental sensor, at least an environmental parameter of a cabin within which the flight crew member is housed;

determining, using a computing device communicatively connected to the at least an exhalation sensor, the first processor of the at least an inhalation sensor, and the at least an environmental sensor, a likelihood of atelectasis for the flight crew member as a function of each of the at least an exhalation parameter, the at least an inhalation parameter, and the at least an environmental parameter, wherein determining the likelihood of atelectasis comprises comparing the at least an environmental parameter to an environmental parameter threshold;

generating, using the computing device, a dosing schedule as a function of the likelihood of atelectasis;

generating, using the computing device, a recompression schedule as a function of the likelihood of atelectasis using at least a machine-learning process;

generating, using the computing device, an auditory coaching comprising instructions to recover from atelectasis as a function of the likelihood of atelectasis and the dosing schedule and the recompression schedule; and communicating, using the computing device, the auditory coaching to the flight crew member using at least a user interface.

9. The method of claim 8, further comprising:

measuring, using an accelerometer, G-force affecting the flight crew member; and wherein determining the likelihood of atelectasis comprises comparing the measured G-force with a G-force threshold.

10. The method of claim 8, further comprising communicating, using the at least a user interface, an alert to the flight crew member as a function of the likelihood of atelectasis.

11. The method of claim 10, wherein the alert comprises a message configured to communicate at least a portion of the dosing schedule.

12. The method of claim 8, wherein the at least an exhalation parameter comprises expirate volume.

13. The method of claim 8, wherein the at least an exhalation parameter comprises expirate carbon dioxide concentration.

14. The method of claim 8, wherein the at least an inhalation parameter comprises inspirate volume.

* * * * *